United States Patent
Nishimura et al.

(10) Patent No.: US 10,241,038 B2
(45) Date of Patent: Mar. 26, 2019

(54) SPECTROPHOTOMETER AND SPECTROPHOTOMETRY METHOD

(71) Applicant: HORIBA, Ltd., Kyoto (JP)

(72) Inventors: Katsumi Nishimura, Kyoto (JP); Shigeru Nakatani, Oberusel (DE); Jan Poppe, Oberusel (DE)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 16/118,730

(22) Filed: Aug. 31, 2018

(65) Prior Publication Data
US 2019/0064064 A1    Feb. 28, 2019

(30) Foreign Application Priority Data

Aug. 31, 2017 (JP) .................. 2017-166784

(51) Int. Cl.
*G01N 21/25* (2006.01)
*G01N 21/3504* (2014.01)
(Continued)

(52) U.S. Cl.
CPC ......... *G01N 21/3504* (2013.01); *G01N 21/25* (2013.01); *G01N 21/49* (2013.01);
(Continued)

(58) Field of Classification Search
CPC .... G01N 21/35; G01N 21/3504; G01N 33/00; G01N 33/66; G01N 33/80; G01N 21/00;
(Continued)

(56) References Cited

U.S. PATENT DOCUMENTS

2007/0054404 A1   3/2007  Huo et al.

2012/0010477 A1*  1/2012  Amano ............... A61B 5/0075
                                                              600/301

FOREIGN PATENT DOCUMENTS

JP    09-101257 A      4/1997
JP    2005-331386 A   12/2005

OTHER PUBLICATIONS

EESR dated Jan. 22, 2019 issued for European Patent Application No. 18 191 934.1, 9 pgs.

* cited by examiner

*Primary Examiner* — Abdullahi Nur
(74) *Attorney, Agent, or Firm* — Brooks Kushman P.C.

(57) ABSTRACT

The present invention responds flexibly to and corrects concentration changes that are caused by changes between the temperature when a correction calibration curve is created and the temperature when a test sample is measured, without having to correct the calibration curve. More specifically, a spectrophotometer measures concentrations of measurement target components contained in a test sample from an optical spectrum obtained by irradiating light onto the test sample, and includes a concentration calculation unit that calculates concentrations of the measurement target components from the optical spectrum using a calibration curve, and a concentration correction unit that, using a temperature correction formula corresponding to a wavelength region or a wavenumber region in which concentrations of the measurement target components are being determined, corrects concentration changes in the measurement target components that accompany temperature differences between a temperature when the calibration curve is created and a temperature when the concentrations are measured.

12 Claims, 4 Drawing Sheets

(51) Int. Cl.
 *G01N 27/26* (2006.01)
 *G01N 33/00* (2006.01)
 *G01N 21/49* (2006.01)
 *G01N 21/35* (2014.01)
(52) U.S. Cl.
 CPC .............. *G01N 27/26* (2013.01); *G01N 33/00* (2013.01); *G01N 2021/3595* (2013.01)
(58) Field of Classification Search
 CPC ........ G01N 21/49; G01N 27/26; G06T 11/20; G06F 19/24; G06F 19/00
 See application file for complete search history.

SPECTROPHOTOMETER AND SPECTROPHOTOMETRY METHOD

CROSS-REFERENCE TO RELATED APPLICATION

This application claims priority to Japanese Application No. 2017-166784, filed Aug. 31, 2017, the disclosure of which is incorporated in its entirety by reference herein.

TECHNICAL FIELD

The present invention relates to a spectrophotometer that employs infrared spectroscopy such as, for example, Fourier-transform infrared spectroscopy, and to a spectrophotometry method.

TECHNICAL BACKGROUND

Conventionally, as is shown in Patent Document 1, an FTIR (Fourier-transform infrared spectroscopy) method is used in order to measure concentrations of measurement target components contained in a test sample such as, for example, exhaust gas or the like.

A spectrophotometer that uses this FTIR method is provided with a measurement cell into which a test sample is introduced, a light irradiation unit that irradiates infrared light onto the measurement cell, and a photodetector that detects an intensity of light transmitted through the measurement cell. This spectrophotometer calculates an optical absorption spectrum of exhaust gas using light intensity signals obtained by the photodetector, and calculates the concentration of the measurement target component from the absorbance of this optical absorption spectrum. Here, when calculating a concentration from the absorbance of the optical absorption spectrum, a calibration curve comparing the absorbance of the optical absorption spectrum with the concentration of the measurement target component shown by this absorbance is used.

In the above-described spectrophotometer, during the measurement of a test sample, the temperature of the measurement cell is adjusted so that it remains constant. If the temperature of the measurement cell differs from the temperature of the measurement cell at the time when the calibration curve was created, then discrepancies occur in the concentrations obtained from the calibration curve.

As is shown in Patent Document 2, a spectrophotometer that corrects the calibration curve at each temperature has been developed in order to reduce discrepancies caused by these temperature changes. More specifically, using the same sample, this spectrophotometer measures a spectrum in advance at a reference temperature and at a different temperature from the reference temperature, and thereby determines a difference spectrum thereof. By then modifying the difference spectrum that has been multiplied by a coefficient in accordance with the temperature changes in the sample such that it is set to the measurement spectrum, the difference spectrum is converted into an equivalent spectrum to the spectrum measured at the reference temperature. The spectrophotometer then corrects the calibration curve calculation results obtained from temperature changes in the sample.

DOCUMENTS OF THE PRIOR ART

Patent Documents

[Patent document 1] Japanese Unexamined Patent Application (JP-A) No. H9-101257

[Patent document 2] Japanese Unexamined Patent Application (JP-A) No. 2005-331386

DISCLOSURE OF THE INVENTION

Problems to be Solved by the Invention

The present invention was therefore conceived in order to comprehensively solve the above-described problems, and was conceived not with the idea of correcting the calibration curve, but with the idea of correcting concentrations obtained from the calibration curve using temperature.

Here, using an equation of state for a gas, because the concentrations of measurement target components decrease as the absolute temperature thereof increases, correcting measurement discrepancies in concentrations obtained from a calibration curve using a correction formula in which the post-correction concentration increases as the absolute temperature increases may be considered.

The inventors of the present application measured the concentrations of $CO_2$, $CO$, $NO$, and $C_3H_8$ when the temperature of a measurement cell was changed from 100° C. to 190° C. The calibration curve used at this time was created using the measurement cell when the temperature thereof was 180° C.

The changes in the concentration of each gas component at this time are shown in FIG. 3. It was found that, as is shown in FIG. 3, the $CO_2$ concentration could not be corrected by means of a correction formula that uses an equation of state for a gas that changes proportionally to the absolute temperature. It was also found that the NO concentration and the $C_3H_8$ concentration exhibited the same type of behavior depending on the temperature range.

When the test samples have high concentrations, because the optical absorption spectrum becomes saturated (i.e., peaks out), it is thought that the aforementioned behaviors may be due to the fact that the absorption of a wavelength band or wavenumber band having a small degree of absorbance located at the edge regions of the absorption band in the optical absorption spectrum is used. More specifically, in simulation results, in a central region of the absorption band in the optical absorption spectrum, the intensity decreases as the temperature increases according to conventional theory. However, in edge regions at a distance from the central regions, the results show that the intensity increases as the temperature increases. It is thought that the reason for this phenomenon is that, as is shown in FIG. 4, the existence probabilities when several rotation states having different energy levels are present change depending on the temperature.

In this manner, it is a principal object of the present invention to flexibly deal with and correct concentration changes that are caused by changes between the temperature when a correction calibration curve is created and the temperature when a test sample is measured, without having to rely on corrections made using an equation of state for a gas.

Means for Solving the Problem

In other words, a spectrophotometer according to the present invention is a spectrophotometer that measures concentrations of measurement target components contained in a test sample from an optical spectrum obtained by irradiating light onto the test sample, and is provided with a concentration calculation unit that calculates concentrations of the measurement target components from the optical spectrum using a calibration curve, and a concentration correction unit that, using a temperature correction formula that corresponds to a wavelength region or a wavenumber region in which concentrations of the measurement target components are being determined, corrects concentration changes in the measurement target components that accompany temperature differences between a temperature when the calibration curve is created and a temperature when the concentrations are measured.

Moreover, a spectrophotometry method according to the present invention is a spectrophotometry method in which concentrations of measurement target components contained in a test sample are measured from an optical spectrum obtained by irradiating light onto the test sample, comprising a concentration calculation step in which concentrations of the measurement target components are calculated from the optical spectrum using a calibration curve, and a concentration correction step in which concentration changes in the measurement target components that accompany temperature differences between a temperature when the calibration curve is created and a temperature when the concentrations are measured are corrected using a temperature correction formula that corresponds to a wavelength region or a wavenumber region in which concentrations of the measurement target components are being determined.

According to the above-described invention, because concentrations of measurement target components are corrected using a temperature correction formula that corrects an amount of change in a temperature when a concentration is measured compared to a temperature when a calibration curve was created, concentrations of measurement target components can be corrected without the calibration curve having to be corrected. Moreover, by creating a temperature correction formula in advance for each measurement target component, corrections can be made so as to correspond to any increase or decrease behavior in the concentration of the measurement target components that are generated by increases or decreases in the absolute temperature. Furthermore, as a consequence of this, correcting concentrations of measurement target components can be performed in real time.

In an optical spectrum there are wavelength regions or wavenumber regions where absorbance signals generated by a plurality of components are mutually superimposed, and there are also wavelength regions or wavenumber regions where peak intensity becomes saturated. In order to reduce the effects of these, and perform accurate measurements of concentrations, the concentration calculation unit is formed so as to calculate concentrations of the measurement target components using predetermined wavelength regions or wavenumber regions in the optical spectrum. At this time, in order to perform temperature corrections accurately, it is desirable that the concentration correction unit use a temperature correction formula that corresponds to the wavelength region or wavenumber region in which the concentrations of the measurement target components are being determined.

The wavelength region or wavenumber region used when concentrations of measurement target components are calculated by the concentration calculation unit vary depending on the type of the measurement target components and the measurement range of the measurement target components. Because of this, in order for temperature correction to be performed accurately, it is desirable that the concentration correction unit update the temperature correction formula in accordance with the type of the measurement target components or the measurement range of the measurement target components.

It is also desirable that the concentration calculation unit calculate concentrations of a plurality of measurement target components using multivariate analysis, and that the concentration correction unit correct the concentration of each measurement target component using the temperature correction formula set for each one of the plurality of measurement target components.

It is also desirable that, in order to favorably correct concentrations of measurement target components that exhibit behavior that cannot be corrected by means of correction that employs an equation of state for a gas, the temperature correction formula output progressively smaller values as the temperature increases. At this time, the temperature correction formula is used to correct changes in energy levels that are caused by the temperature of the measurement target components.

When the test sample is a gas, changes in energy levels that are caused by the temperature of the measurement target components tend to occur easily, so that the effects obtained when the present invention is applied are even more conspicuous.

As a specific embodiment for calculating the temperature correction formula automatically, it is desirable that there be further provided a standard spectrum acquisition unit that acquires respective optical spectra of a plurality of temperatures from standard test samples having known concentrations, and a correction formula creation unit that calculates the temperature correction formula from the standard spectra of the plurality of temperatures.

The wavelength region or wavenumber region used by the concentration calculation unit is updated depending on whether or not interference components are present, the type of measurement target components, and the measurement range and the like. In order to make accurate corrections corresponding to these updates, it is desirable that, when the wavelength region or wavenumber region used for the concentration calculation performed by the concentration calculation unit is updated, the correction formula creation unit update the temperature correction formula so that it corresponds to the updated wavelength region or wavenumber region.

In a spectrophotometer, processing to update the calibration curve is performed at regular intervals. In order to update the correction formula so that it matches the update processing for the calibration curve, and thereby standardize the various processings, it is desirable that the correction formula creation unit calculate the temperature correction formula from the standard spectra obtained at the time the calibration curve was created.

Effects of the Invention

According to the present invention which is formed in the above-described manner, it is possible, even for components that are difficult to correct simply by performing calculations using an equation of state for a gas, to correct temperature effects which differ for each component by flexibly dealing with concentration changes that are caused by changes between the temperature when a calibration curve was created and the temperature when a test sample was measured, without having to correct the calibration curve.

BEST EMBODIMENTS FOR IMPLEMENTING THE INVENTION

Hereinafter, an embodiment of an infrared spectrophotometer according to the present invention will be described with reference to the drawings.

An infrared spectrophotometer 100 according to the present embodiment is an exhaust gas analyzer that, for example, measures, as time series data, concentrations of a plurality of components that are contained in exhaust gas, which is serving as a test sample, that is emitted from an internal combustion engine of an automobile or the like.

Figure 1:
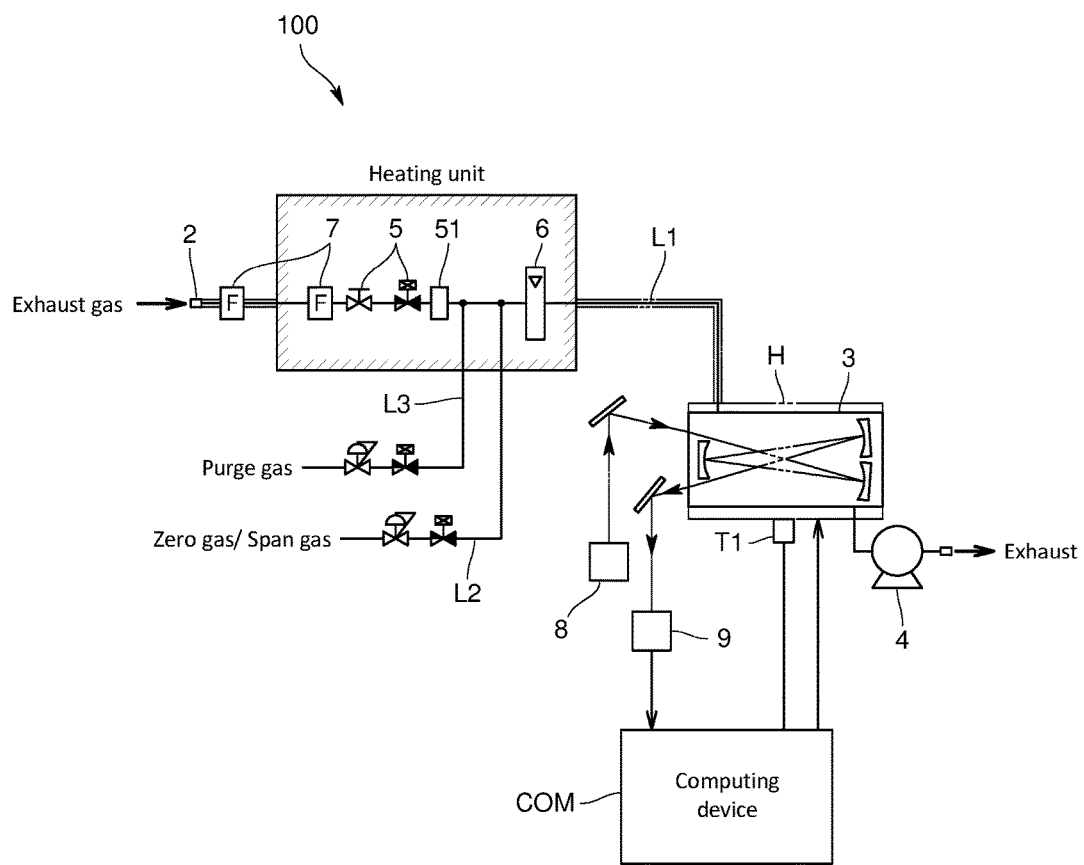
FIG. 1 is a schematic view showing the structure of an infrared spectrophotometer according to the present embodiment.

More specifically, as is shown in FIG. 1, this infrared spectrophotometer 100 collects, for example, either a portion of or all of the exhaust gas emitted from a tailpipe of an automobile using a test sample collecting unit 2, and then, without diluting it, introduces the exhaust gas collected by the test sample collecting unit 2 into a measurement cell 3, and then measures the respective concentrations of a plurality of components such as, for example, carbon monoxide (CO), carbon dioxide ($CO_2$), nitric oxide (NO), nitrogen dioxide ($NO_2$), nitrogen oxide ($NO_X$), and water ($H_2O$) and the like that are contained in the exhaust gas using an FTIR method. A temperature control mechanism H such as a heater or the like that controls the temperature of the measurement cell 3 and of the gas inside the measurement cell 3 is provided peripherally to the measurement cell 3. The temperature of the measurement cell 3 is detected by a temperature sensor T1. This temperature control mechanism H is controlled by a computing device COM based on temperatures detected by the temperature sensor T1 such that a predetermined temperature is obtained.

Moreover, in the infrared spectrophotometer 100, a suction pump 4 that is used to introduce the exhaust gas into the measurement cell 3 is provided on a downstream side of the measurement cell 3 on an exhaust gas line L1 on which the measurement cell 3 is provided. In addition to these, valves 5 that adjust the flow rate of the exhaust gas, an orifice 51, a flowmeter 6 that measures the flow rate of the exhaust gas, and filters 7 that remove dust particles from the exhaust gas, and the like are also provided on the exhaust gas line L1. Moreover, a calibration gas supply line L2 that supplies the measurement cell 3 with zero gas or span gas that is used to calibrate a photodetector 9, and a purge gas line L3 that is used to purify the exhaust gas line L1 or the measurement cell 3 are also connected to the exhaust gas line L1 or the measurement cell 3.

Furthermore, the infrared spectrophotometer 100 is also provided with a light irradiation unit 8 that irradiates interfered infrared light onto the measurement cell 3, and the photodetector 9 that detects an intensity of the light that is emitted after being transmitted through the measurement cell 3. The computing device COM of the infrared spectrophotometer 100 calculates an optical absorption spectrum in the optical spectrum of the exhaust gas using light intensity signals obtained by the photodetector 9, and calculates the concentrations of a plurality of measurement target components from the absorbance of a predetermined wavelength region or wavenumber region in this optical absorption spectrum.

Figure 2:
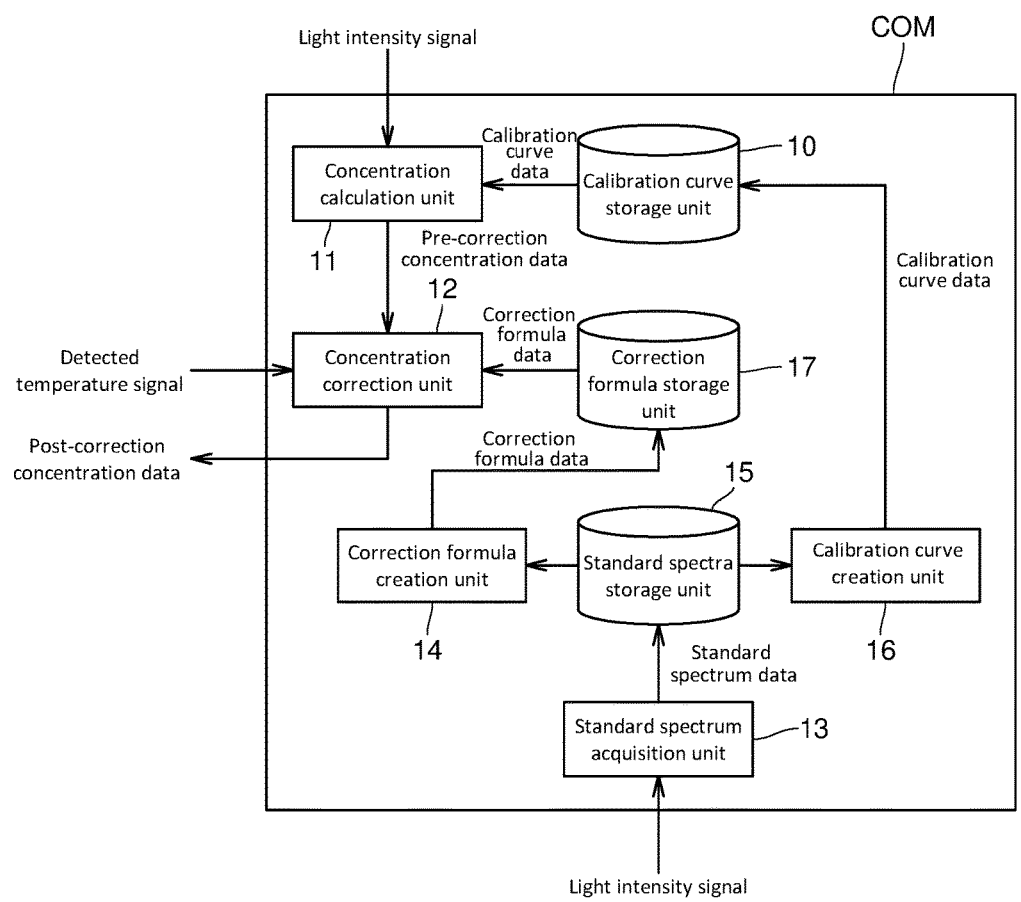
FIG. 2 is a functional block diagram showing an information processing device of the same embodiment.

As is shown in FIG. 2, the computing device COM of the infrared spectrophotometer 100 is provided with a calibration curve storage unit 10 that stores calibration curve data showing relationships between absorbances of measurement target components and concentrations of measurement target components, a concentration calculation unit 11 that calculates concentrations of measurement target components from optical absorption spectra and calibration curves shown by the calibration curve data, and a concentration correction unit 12 that corrects concentrations of measurement target components using temperature correction formulas.

The calibration curve storage unit 10 stores calibration curve data created at a predetermined temperature (for example, at a reference temperature). Relationships between the concentrations of each component (formed by a plurality of representative values, for example, in the case of CO, concentrations of 2%, 4%, 6%, 8%, and the like) and the respective absorbances thereof are determined on this calibration curve. This calibration curve data can be created by a calibration curve creation unit 16 (described below). Note that the calibration curve data may be in the form of an arithmetical expression, or may be in tabular form.

The concentration calculation unit 11 acquires light intensity signals from the photodetector 9, and also acquires calibration curve data from the calibration curve storage unit 10, and then calculates optical absorption spectra from the light intensity signals, and then uses multivariate analysis to calculate the concentrations of each measurement target component from the absorbance in a predetermined wavelength region or wavenumber region of the relevant optical absorption spectrum, and from the calibration curve shown by the calibration curve data.

The concentration correction unit 12 uses a temperature correction formula set for each relevant measurement target component to perform temperature correction on the concentrations of each measurement target component obtained by the concentration calculation unit 11 based on temperatures detected by the temperature sensor T1. The correction formula data showing the temperature correction formula is stored in a correction formula storage unit 17.

Here, temperature correction formulas are used to correct changes in the concentrations of the measurement target components that accompany temperature differences between the temperature of the measurement cell 3 at the time when the calibration curve was created, and the temperature of the measurement cell 3 at the time when the concentration was measured. Temperature correction formulas are determined in accordance with the wavelength region or the wavenumber region in which the concentrations of the measurement target components are being determined. The temperature correction formulas of the present embodiment are determined from a polynomial in the form of a temperature-concentration relational formula (for example, the formula given below in Equation 2).

More specifically, the following formulas can be considered as examples of temperature-concentration relational formulas. Namely, (1) a formula in which the concentration increases as the absolute temperature increases, (2) a formula in which the concentration decreases as the absolute temperature increases, and (3) a formula in which, within a predetermined range, the concentration increases as the absolute temperature increases, while once that predetermined range is exceeded, the concentration decreases as the absolute temperature increases.

For example, the temperature-concentration relational formula for $CO_2$ is a formula in which the concentration increases steadily as the temperature increases. Moreover, the temperature-concentration relational formula for CO is a formula in which the concentration decreases steadily as the temperature increases. Furthermore, the temperature-concentration relational formula for NO is a formula in which the concentration switches from a steady increase as the temperature increases to a steady decrease. Note that because it may be thought that the change in concentration arising from the change in temperature in the case of $CO_2$ is caused by a change in the energy level that is generated by the change in temperature, the temperature correction formula for $CO_2$ can be described as a formula to correct the change in the energy level that is generated by the change in temperature.

In order to create this temperature correction formula, the computing device COM of the infrared spectrophotometer 100 is further provided with a standard spectrum acquisition unit 13 that acquires optical absorbance spectra for each of a plurality of temperatures from standard test samples having known concentrations, and a correction formula creation unit 14 that creates temperature correction formulas from the standard spectra of the plurality of temperatures.

The standard spectrum acquisition unit 13 acquires a plurality of sets of spectrum data that show the respective standard spectra of a plurality of temperatures of a standard test sample at the time when a calibration curve was created or the like, and stores these sets of spectrum data in a standard spectra storage unit 15. Here, the standard spectrum data may be obtained as a result of the standard spectrum acquisition unit 13 acquiring light intensity signals from the photodetector 9 and then calculating the standard spectrum data, or may be obtained as a result of a separate functional block such as the concentration calculation unit 11 acquiring the light intensity signal from the photodetector 9 at the time when the calibration curve was created, and then calculating the standard spectrum data, which is then received by the standard spectrum acquisition unit 13.

The correction formula creation unit 14 creates correction formula data showing temperature correction formulas that correspond to the respective wavelength region or wavenumber region used by the concentration calculation unit 11 to calculate the concentrations of the plurality of measurement target components. Additionally, when the wavelength region or wavenumber region used in the calculations for the respective measurement target components by the concentration calculation unit 11 is updated, the correction formula creation unit 14 creates updated correction formula data showing temperature correction formulas that correspond to the relevant updated wavelength region or wavenumber region.

Next, processing to calculate a temperature correction formula which is performed in conjunction with the creation of the calibration curve in the infrared spectrophotometer 100 will be described.

A standard test sample (i.e., calibration gas) having a known concentration is introduced into the measurement cell 3 whose temperature has been adjusted to a predetermined reference temperature (for example, 100° C.). In this state, infrared light is irradiated onto the measurement cell 3 from the light irradiation unit 8, and light that has been transmitted through the measurement cell 3 is detected by the photodetector 9. The standard spectrum acquisition unit 13 or the like then calculates a standard spectrum from a light intensity signal output from the photodetector 9, and stores this in the standard spectra storage unit 15. Here, the temperature of the measurement cell 3 into which the calibration gas has been introduced is then raised from the reference temperature by, for example, 10° C. each time, and the standard spectrum data at each temperature is also acquired.

Next, the calibration curve creation unit 16 of the spectrophotometer 100 decides the wavelength region or wavenumber region to be used when calculating the concentration of each measurement target component from the standard spectrum data obtained at the reference temperature, and creates calibration curve data showing a calibration curve using the absorbance in the relevant wavelength region and wavenumber region.

Furthermore, the concentration calculation unit 11 then determines the concentrations of the measurement target components at each temperature in the relevant wavelength region and wavenumber region from the calibration curve data and the standard spectrum data obtained at the other temperatures. In addition, the correction formula creation unit 14 creates correction formula data showing a temperature correction formula from the concentrations the measurement target components at each temperature obtained from the standard spectrum data, and from the known concentrations of the measurement target components of the calibration gas.

Hereinafter, the temperature correction formula used by the concentration correction unit 12 will be described. The temperature correction formula used by the concentration correction unit 12 can be shown by the following.

$$C_{comp} = \frac{C_{unk}}{a_3 T^3 + a_2 T^2 + a_1 T + a_0} \quad \text{[Equation 1]}$$

Here, $C_{comp}$ is the post-correction concentration of the measurement target components, and $C_{unk}$ is the pre-correction concentration of the measurement target components. The coefficients $a_0 \sim a_3$ are fitting parameters.

This formula (Equation 1) can be determined in the following manner.

Figure 3:
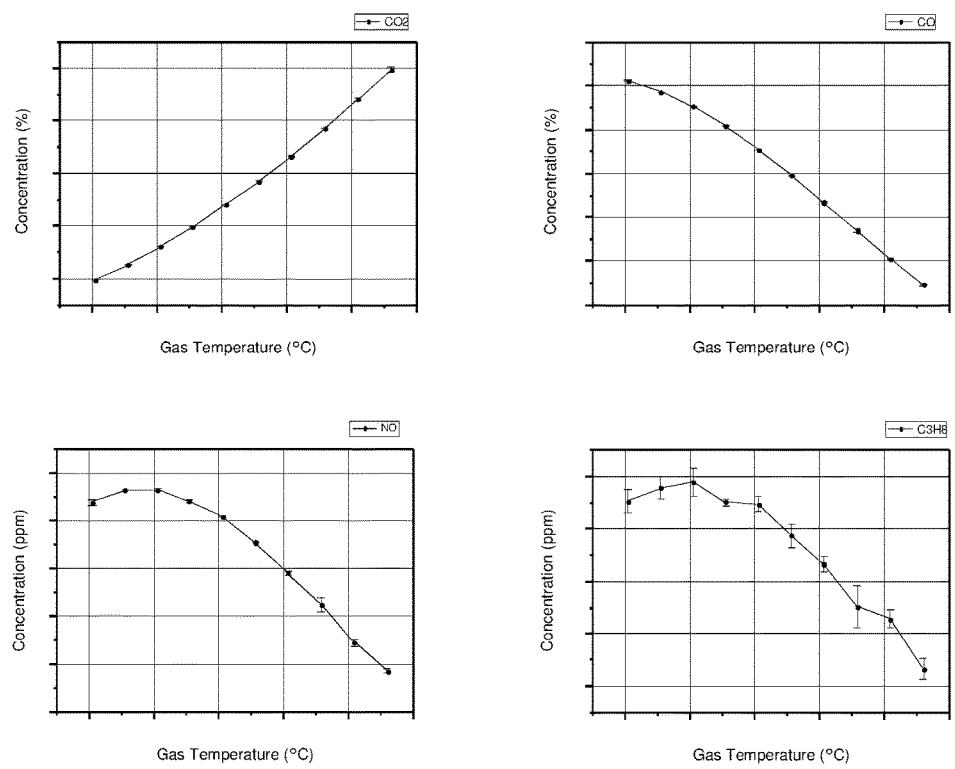
FIG. 3 depicts graphs showing relationships between the absolute temperature and the concentration of each gas component.
Figure 4:
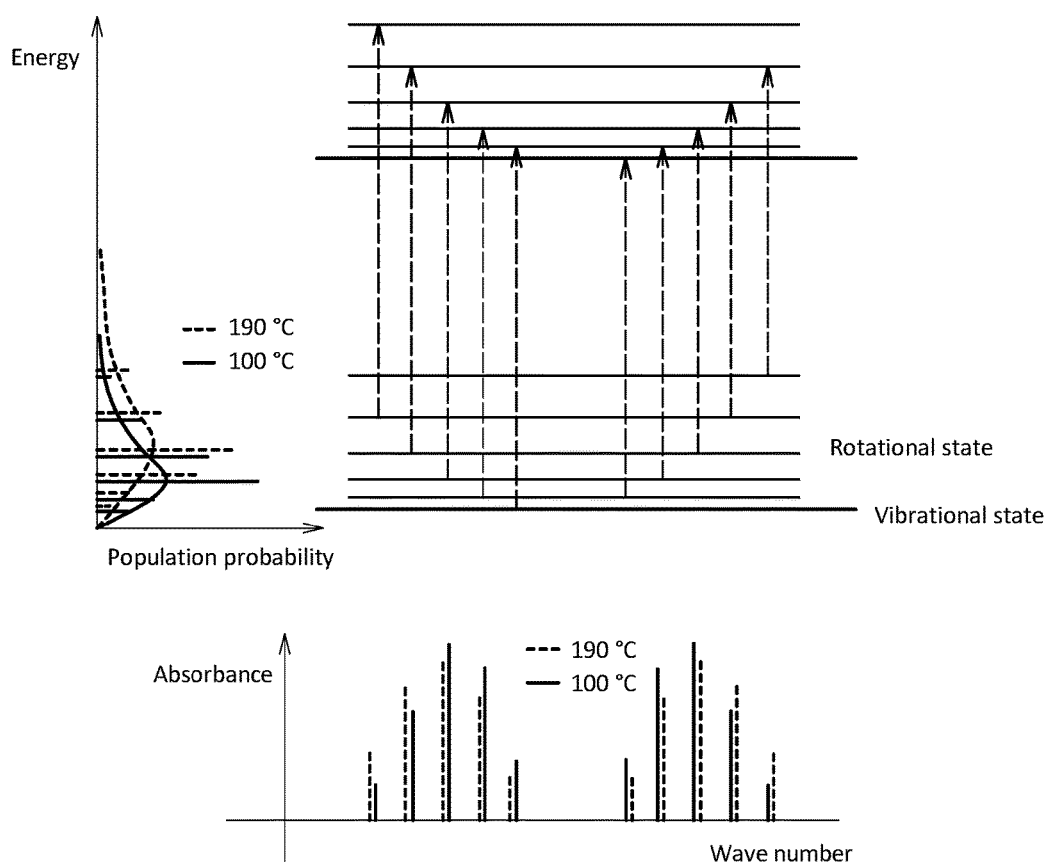
FIG. 4 is a view showing changes in energy level that accompany changes in temperature.

If fitting is performed using graphs (these are the graphs shown in FIG. 3 in which the horizontal axis shows temperature while the vertical axis shows concentration) of the concentrations of measurement target components at each temperature obtained using a calibration gas having a known concentration, then the following relational expression (i.e., a temperature—concentration relational expression) is obtained. Note that in the following a third-order equation is used, however, it is also possible for a fourth-order equation or greater, or a first-order or second-order equation to be used.

$$\frac{C_{bottle\_meas}}{C_{bottle}} = a_3 T^3 + a_2 T^2 + a_1 T + a_0 \quad \text{[Equation 2]}$$

Here, $C_{bottle}$ is the known concentration of the measurement target compounds in the calibration gas. Moreover, $C_{bottle\_meas}$ is the measurement value of the measurement target components in the calibration gas at each temperature. The coefficients $a_0 \sim a_3$ are fitting parameters.

Because this relational expression is also valid when measuring measurement target components having unknown concentrations, the relationship between the post-correction concentration $C_{comp}$, and the pre-correction concentration $G_{unk}$ is as follows.

$$\frac{C_{unk}}{C_{comp}} = a_3 T^3 + a_2 T^2 + a_1 T + a_0 \qquad \text{[Equation 3]}$$

The above-described formula (Equation 1) can be obtained by transforming this relational expression (i.e., a temperature—concentration relational expression).

The correction formula creation unit 14 creates correction formula data by calculating the coefficients $a_0$~$a_3$ for each one of the plurality of measurement target components contained in the exhaust gas. The correction formula data showing the coefficients $a_0$~$a_3$ obtained by the correction formula creation unit 14 is then stored in the correction formula storage unit 17.

According to the infrared spectrophotometer 100 of the present embodiment which is formed in this manner, because the concentrations of measurement target components are corrected using a temperature correction formula that corrects an amount of change between the temperature at the time when a calibration curve was created and the temperature at the time when a concentration was measured, it is possible to correct the concentrations of measurement target components without having to correct the calibration curve. Additionally, by creating a temperature correction formula for each measurement target component, corrections can be made so as to correspond to any increase or decrease behavior in the concentrations of the measurement target components that are generated by increases or decreases in the absolute temperature. Furthermore, as a consequence of this, correcting concentrations of measurement target components can be performed in real time.

Note that the present invention is not limited to the above-described embodiment.

For example, in addition to a structure in which a temperature correction formula is determined from standard spectrum data obtained when a calibration curve is created, it is also possible to determine a temperature correction formula from standard spectrum data obtained independently of the calibration curve creation. In this case, it is necessary for the temperature of the measurement cell 3 when the standard spectrum data is acquired to be the same as the temperature when the calibration curve is created.

Moreover, in the above-described embodiment, it is also possible for the concentration correction unit 12 to determine whether or not to perform a temperature correction in accordance with the wavelength region or the wavenumber region in which the concentration of the measurement target components is being determined. For example, it is also possible to correct concentrations using a temperature correction formula not when the wavelength region or wavenumber region is a central region of the absorption band, but only when the wavelength region or wavenumber region is a rise region of an edge region.

Furthermore, it is also possible for the concentration correction unit 12 to correct a concentration using a temperature correction formula only when the concentration of a measurement target component is equal to or greater than a predetermined value.

In the above-described embodiment, it is also possible for the concentration correction unit 12 to update the temperature correction formula in accordance with the measurement range of the measurement target components.

Furthermore, in the above-described embodiment, a structure is employed in which the post-correction concentration is calculated after the measurement values obtained by the concentration calculation unit 11 have only been corrected once, however, it is also possible to employ a structure in which the same type of correction as that performed in the above-described embodiment is additionally performed on concentrations that have already been corrected using a correction formula that uses an equation of state for a gas.

In the above-described embodiment, an analyzer that uses an FTIR method is described, however, an analyzer that uses an NDIR method may also be used.

In the above-described embodiment, an example is described in which temperature correction is performed using the temperature T1 of the measurement cell 3, however, it is also possible to perform the temperature correction using the temperature of the gas inside the measurement cell 3.

Moreover, the spectrophotometer of the present invention is not limited to using infrared light, and a spectrophotometer that uses ultraviolet light or one that uses visible light may also be used.

Moreover, in the above-described embodiment, a case in which the present invention is applied to an exhaust gas analyzer that analyzes exhaust gas emitted from an internal combustion engine is described, however, the present invention may also be applied to an exhaust gas analyzer that analyzes exhaust gas emitted from a factory or a power plant, or to an exhaust gas analyzer that analyzes other types of test sample gas. Furthermore, the test sample is not limited to being a gas, and may be a liquid such as a liquid chemical or the like.

Furthermore, it should be understood that the present invention is not limited to the above-described embodiment, and that various modifications and the like may be made thereto insofar as they do not depart from the spirit or scope of the present invention.

DESCRIPTION OF THE REFERENCE NUMERALS

100 . . . Infrared spectrophotometer
11 . . . Concentration Calculation Unit
12 . . . Concentration Correction Unit
13 . . . Standard Spectrum Acquisition Unit
14 . . . Correction Formula Creation Unit

What is claimed is:

1. A spectrophotometer that measures concentrations of measurement target components contained in a test sample from an optical spectrum obtained by irradiating light onto the test sample, comprising:
    a concentration calculation unit that calculates concentrations of the measurement target components from the optical spectrum using a calibration curve; and
    a concentration correction unit that, using a temperature correction formula that corresponds to a wavelength region or a wavenumber region in which concentrations of the measurement target components are being determined, corrects concentration changes in the measurement target components that accompany temperature differences between a temperature when the calibration curve is created and a temperature when the concentrations are measured.

2. The spectrophotometer according to claim 1, wherein the concentration correction unit updates the temperature correction formula in accordance with the type of the measurement target components or the measurement range of the measurement target components.

3. The spectrophotometer according to claim 1, wherein the concentration calculation unit calculates concentrations of a plurality of measurement target components using multivariate analysis, and
the concentration correction unit corrects the concentration of each measurement target component using the temperature correction formula set for each one of the plurality of measurement target components.

4. The spectrophotometer according to claim 1, wherein the temperature correction formula is a formula that outputs progressively smaller values as the temperature increases.

5. The spectrophotometer according to claim 1, wherein the test sample is a gas, and
the temperature correction formula is used to correct changes in energy levels that are caused by the temperature of the measurement target components.

6. The spectrophotometer according to claim 1, wherein the concentration correction unit corrects concentrations of the measurement target components using the temperature correction formula only when the wavelength region or wavenumber region in which the concentration of the measurement target components is being determined is a different region from a central region of the absorption band.

7. The spectrophotometer according to claim 1, further comprising:
a standard spectrum acquisition unit that acquires respective optical spectra of a plurality of temperatures from standard test samples having known concentrations; and
a correction formula creation unit that creates the temperature correction formula from the standard spectra of the plurality of temperatures.

8. The spectrophotometer according to claim 7, wherein, when the wavelength region or wavenumber region used for the concentration calculation performed by the concentration calculation unit is updated, the correction formula creation unit updates the temperature correction formula so as to correspond to the relevant updated wavelength region or wavenumber region.

9. The spectrophotometer according to claim 7, wherein the correction formula creation unit calculates the temperature correction formula from the standard spectra obtained at the time the calibration curve was created.

10. A spectrophotometer that measures concentrations of measurement target components contained in a test sample from an optical spectrum obtained by irradiating light onto the test sample, comprising:

a concentration calculation unit that calculates concentrations of the measurement target components from the optical spectrum using a calibration curve; and a concentration correction unit that, using a predetermined temperature correction formula, corrects concentration changes in the measurement target components that accompany temperature differences between a temperature when the calibration curve is created and a temperature when the concentrations are measured.

11. A spectrophotometry method in which concentrations of measurement target components contained in a test sample are measured from an optical spectrum obtained by irradiating light onto the test sample, comprising:

a concentration calculation step in which concentrations of the measurement target components are calculated from the optical spectrum using a calibration curve; and a concentration correction step in which concentration changes in the measurement target components that accompany temperature differences between a temperature when the calibration curve is created and a temperature when the concentrations are measured are corrected using a temperature correction formula that corresponds to a wavelength region or a wavenumber region in which concentrations of the measurement target components are being determined.

12. A non-transitory computer-readable recording medium storing a spectroscopic analysis program that is used in a spectrophotometer that measures concentrations of measurement target components contained in a test sample from an optical spectrum obtained by irradiating light onto the test sample, and that provides a computer with:

a function of a concentration calculation unit that calculates concentrations of the measurement target components from the optical spectrum using a calibration curve; and a function of a concentration correction unit that, using a temperature correction formula that corresponds to a wavelength region or a wavenumber region in which concentrations of the measurement target components are being determined, corrects concentration changes in the measurement target components that accompany temperature differences between a temperature when the calibration curve is created and a temperature when the concentrations are measured.

* * * * *